United States Patent [19]

Murdock et al.

[11] 4,138,415
[45] Feb. 6, 1979

[54] 1,4-BIS(AMINOALKYLAMINO)-ANTHRAQUINONES AND LEUCO DERIVATIVES THEREOF

[75] Inventors: Keith C. Murdock; Ralph G. Child, both of Pearl River, N.Y.

[73] Assignee: American Cyanamid Company, Stamford, Conn.

[21] Appl. No.: 903,292

[22] Filed: May 5, 1978

[51] Int. Cl.$^2$ .................. C07C 97/26; C09B 1/515
[52] U.S. Cl. ................... 260/378; 260/380; 252/438
[58] Field of Search .................. 260/378, 380

[56] References Cited

U.S. PATENT DOCUMENTS

| 3,467,483 | 9/1969 | Bugaut et al. | 260/378 |
| 3,646,072 | 2/1972 | James et al. | 260/380 |

FOREIGN PATENT DOCUMENTS

| 659168 | 1965 | Belgium | 260/380 |
| 1157506 | 1969 | United Kingdom | 260/380 |

OTHER PUBLICATIONS

Chemical Abstract, vol. 69, No. 2933C, p. 287, 1968, "The Reaction of Leucoquinizarins with Alkylenediamines," 1968, Greenhalgh et al.

*Primary Examiner*—Allen B. Curtis
*Assistant Examiner*—Raymond Covington
*Attorney, Agent, or Firm*—Edward A. Conroy, Jr.

[57] ABSTRACT

This disclosure describes 1,4-bis(substituted-amino)-5,6-dihydroxyanthraquinones and 1,4,5-tris(substituted-amino)-8-hydroxyanthraquinones useful as chelating agents, as curing catalysts for epoxy resins, and for inhibiting the growth of transplanted mouse tumors.

6 Claims, No Drawings

1,4-BIS(AMINOALKYLAMINO)-ANTHRAQUINONES AND LEUCO DERIVATIVES THEREOF

BRIEF SUMMARY OF THE INVENTION

This invention relates to new organic compounds and, more particularly, is concerned with novel anthraquinones which may be represented by the following structural formula:

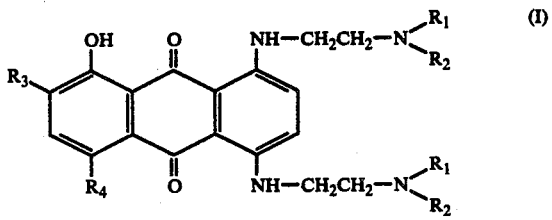

wherein $R_1$ and $R_2$ are each individually selected from the group consisting of hydrogen, methyl, ethyl and 2-hydroxyethyl; $R_3$ is hydrogen or hydroxy; and $R_4$ is hydrogen or a moiety of the formula:

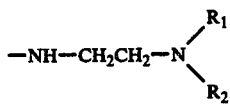

wherein $R_1$ and $R_2$ are as hereinabove defined with the proviso that one of $R_3$ and $R_4$ must be hydrogen but $R_3$ and $R_4$ may not both be hydrogen. Also included within the purview of the present invention are the leuco bases and tautomers thereof which may be represented by the following general formulae:

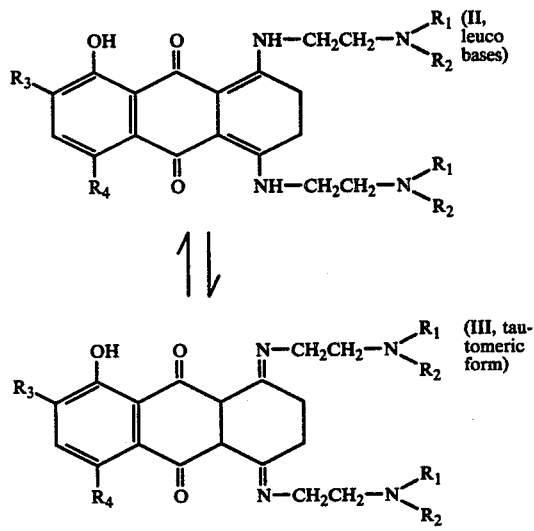

wherein $R_1$, $R_2$, $R_3$ and $R_4$ are as hereinabove defined.

DETAILED DESCRIPTION OF THE INVENTION

The novel compounds of the present invention are obtainable as reddish brown to blue black crystalline materials having characteristic melting points and absorption spectra and which may be purified by leaching with lower alkanols since the free bases are insoluble in water and some of them are insoluble in most organic solvents.

The organic bases of this invention (I, II and III) form non-toxic acid-addition salts with a variety of pharmacologically acceptable organic and inorganic salt-forming reagents. Thus, acid-addition salts, formed by admixture of the organic free base with two or three equivalents of an acid, suitably in a neutral solvent, are formed with such acids as sulfuric, phosphoric, hydrochloric, hydrobromic, sulfamic, citric, lactic, malic, succinic, tartaric, acetic, benzoic, gluconic, ascorbic, and the like. Quaternary ammonium salts may be formed by reaction of the free bases with two or three equivalents of a variety of organic esters of sulfuric, hydrohalic and aromatic sulfonic acids. For purposes of this invention the free bases are equivalent to their non-toxic acid-addition salts. The acid-addition salts of the organic bases of the present invention are, in general, crystalline solids, relatively soluble in water, methanol and ethanol but relatively insoluble in non-polar organic solvents such as diethyl ether, benzene, toluene, and the like.

The novel compounds of the present invention may be readily prepared in accordance with the following reaction scheme:

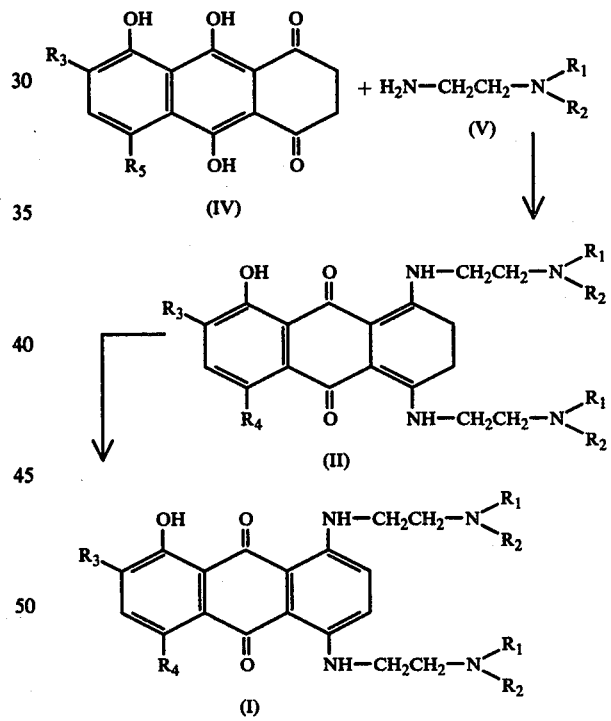

wherein $R_5$ is hydrogen or hydroxy and $R_3$ and $R_4$ are as hereinabove defined with the proviso that one of $R_3$ and $R_5$ must be hydrogen but $R_3$ and $R_5$ may not both be hydrogen. In accordance with this reaction scheme, leuco-1,4,5,6-tetrahydroxyanthraquinone (IV) or leuco-1,4,5,8-tetrahydroxyanthraquinone (IV) is condensed with an appropriately substituted ethylene diamine (V) in the presence of N,N,N',N'-tetramethylethylene diamine at from about 40° C. to about 60° C. under an atmosphere of nitrogen for several hours to produce the corresponding leuco bases (II). The leuco bases (II) may be readily oxidized to the fully aromatic derivatives (I) by a variety of methods such as air oxidation or treatment with hot nitrobenzene, or treatment with chloranil, hydrogen peroxide, or sodium perborate.

The novel compounds described herein are useful as chelating, complexing or sequestering agents. The complexes formed with polyvalent metal ions are particularly stable and usually soluble in various organic solvents. These properties, of course, render them useful for a variety of purposes wherein metal ion contamination presents a problem; e.g., as stabilizers in various organic systems such as saturated and unsaturated lubricating oils and hydrocarbons, fatty acids and waxes, wherein transition metal ion contamination accelerates oxidative deterioration and color formation. They are further useful in analyses of polyvalent metal ions which may be complexed or extracted by these materials and as metal carriers. Other uses common to sequestering agents are also apparent for these compounds. In addition, the leuco bases (II) are useful as intermediates in the preparation of the fully aromatic derivatives (I).

The new compounds of the present invention are useful curing catalysts for epoxy resins. As is well known to the art, these resins are condensates of epichlorohydrin and a polyhydric alcohol, i.e., bisphenol. The curing agents have the property of changing a fusible thermosetting resinous material to an infusible thermoset resinous material. The resinous compositions are useful in a variety of applications such as molding, laminating, etc. The new compounds may be used in curing epoxy resins by methods known to the art. Thus the compounds may be added to the epoxy resin and the mixture heated to effect curing of the hard resinous products. For this purpose temperatures of from 150-180° C. may be used.

The novel compounds of the present invention also possess the property of inhibiting the growth of transplanted mouse tumors as established by the following tests.

LYMPHOCYTIC LEUKEMIA P388 TEST

The animals used are DBA/2 mice all of one sex, weighing a minimum of 17 g. and all within a 3 gram weight range. There are 5 or 6 animals per test group. The tumor transplant is by intraperitoneal injection of 0.1 ml. of dilute ascitic fluid containing $10^6$ cells of lymphocytic leukemia P388. The test compounds are administered intraperitoneally on days one, 5 and 9 (relative to tumor inoculation) at various doses. The animals are weighed and survivors are recorded on a regular basis for 30 days. The median survival time and the ratio of survival time for treated (T)/control (C) animals are calculated. The positive control compound is 5-fluorouracil given as a 60 mg./kg. injection. The results of this test with representative compounds of the present invention appear in Table I. The criterion for efficacy is T/C × 100 ≧125%.

TABLE I

| Lymphocytic Leukemia P388 Test | | | |
|---|---|---|---|
| Compound | Dose (mg./kg.) | Median Survival (Days) | T/C × 100 (Percent) |
| 1,4,5-Tris[(2-amino-ethyl)amino]-8-hydroxy-anthraquinone | 12 | 15.0 | 130 |
|  | 6 | 15.0 | 130 |
|  | 3 | 15.0 | 130 |
|  | 1.5 | 15.0 | 130 |
| 1,4-Bis[(2-dimethyl-aminoethyl)amino]-5,6-dihydroxyanthraquinone | 50 | 18 | 157 |
|  | 25 | 16 | 139 |
|  | 12 | 16 | 139 |
| Control | 0 | 11.5 | — |

TABLE I-continued

| Lymphocytic Leukemia P388 Test | | | |
|---|---|---|---|
| Compound | Dose (mg./kg.) | Median Survival (Days) | T/C × 100 (Percent) |
| 5-Fluorouracil | 60 | 19.0 | 165 |

MELANOTIC MELANOMA B16

The animals used are C57BL/6 mice, all of the same sex, weighing a minimum of 17 g. and all within a 3 g. weight range. There are normally 10 animals per test group. A one-gram portion of melanotic melanoma B16 tumor is homogenized in 10 ml. of cold balanced salt solution and a 0.5 ml. aliquot of the homogenate is implanted intraperitoneally into each of the test mice. The test compounds are administered intraperitoneally on days one through 9 (relative to tumor inoculation) at various doses. The animals are weighed and survivors are recorded on a regular basis for 60 days. The mediam survival time and the ratio of survival time for treated (T)/control (C) animals are calculated. The positive control compound is 5-fluorouracil given as a 20 mg./kg. injection. The results of this test with representative compounds of the present invention appear in Table II. The criterion for efficacy is T/C × 100 ≧ 125%.

TABLE II

| Melanotic Melanoma B16 Test | | | |
|---|---|---|---|
| Compound | Dose (mg./kg.) | Median Survival (Days) | T/C × 100 (Percent) |
| 1,4,5-Tris[(2-aminoethyl)-amino]-8-hydroxy-anthraquinone | 6 | 26.0 | 163 |
| 1,4-Bis[2-dimethylaminoethyl)amino]-5,6-dihydroxyanthraquinone | 50 | 23 | 153 |
|  | 25 | 24 | 160 |
|  | 12 | 23 | 153 |
|  | 6 | 22.5 | 150 |
| Control | 0 | 16.0 | — |
| 5-Fluorouracil | 20 | 26.5 | 166 |

The invention will be described in greater detail in conjunction with the following specific examples.

EXAMPLE 1

1,4,5-Tris[(2-aminoethyl)amino]-8-hydroxy-anthraquinone

A 100 ml. portion of ethylenediamine is de-aerated by bubbling nitrogen through it for 15 minutes. A 10.97 g. portion of leuco-1,4,5,8-tetrahydroxyanthraquinone is added and the mixture is stirred under nitrogen at 50°–51° C. for one hour. The mixture is cooled and filtered. The unstoppered filtrate is allowed to cool at 10° C. for 2 hours producing a solid which is collected and washed with ethanol, giving 2.25 g. of the desired product as a dark purple solid.

EXAMPLE 2

1,4-Bis[(2-dimethylaminoethyl)amino]-5,6-dihydroxy-anthraquinone

A 30 g. portion of zinc is added portionwise to a boiling mixture of 1.5 liters of glacial acetic acid and 40 ml. of water containing 27.2 g. of 1,4,5,6-tetrahydroxyanthraquinone. The mixture is boiled for 30 minutes, filtered and the filtrate is cooled. The orange-brown crystals which form are collected giving 19.7 g. of leuco-1,4,5,6-tetrahydroxyanthraquinone, mp. 255°–257° C.

A 7.9 g. portion of dimethylaminoethylamine in 75 ml. of tetramethylethylenediamine is heated to 80°–100° C. and deaerated with nitrogen. This mixture is treated portionwise with 8.22 g. of leuco-1,4,5,6-tetrahydroxyanthraquinone with stirring under nitrogen and heated at 90°–100° C. for 6 hours. The mixture is filtered while hot. The filtrate is cooled to 4° C., treated with ether and after standing 48 hours gives a dark blue gum. The supernatant is decanted, treated with twice its volume of ether and cooled giving a blue gum. This supernatant is allowed to stand and is then treated with more ether producing 1.5 g. of the desired final product as a blue solid, mp. 133°–135° C.

EXAMPLE 3

1,4,5-Tris{[2-(2-hydroxyethylamino)ethyl]amino}-8-hydroxyanthraquinone

The reaction between 2-(2-hydroxyethylamino)ethylamine and leuco-1,4,5,8-tetrahydroxyanthraquinone is carried out as in Example 1 to give the title compound.

We claim:

1. A compound selected from the group consisting of those of the formula:

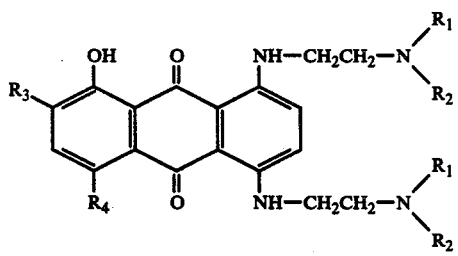

wherein $R_1$ and $R_2$ are each individually selected from the group consisting of hydrogen, methyl, ethyl and 2-hydroxyethyl; $R_3$ is hydrogen or hydroxy; $R_4$ is hydrogen or a moiety of the formula:

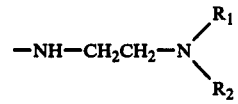

wherein $R_1$ and $R_2$ are as hereinabove defined with the proviso that one of $R_3$ and $R_4$ must be hydrogen but $R_3$ and $R_4$ may not both be hydrogen; and the pharmacologically acceptable acid-addition salts thereof.

2. A compound selected from the group consisting of those of the formula:

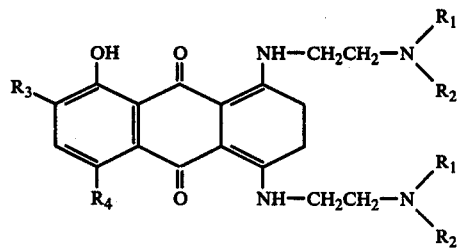

wherein $R_1$ and $R_2$ are each individually selected from the group consisting of hydrogen, methyl, ethyl and 2-hydroxyethyl; $R_3$ is hydrogen or hydroxy; $R_4$ is hydrogen or a moiety of the formula:

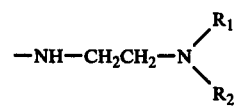

wherein $R_1$ and $R_2$ are as hereinabove defined with the proviso that one of $R_3$ and $R_4$ must be hydrogen but $R_3$ and $R_4$ may not both be hydrogen; the tautomers thereof; and the pharmacologically acceptable acid-addition salts thereof.

3. The compound according to claim 1 wherein $R_1$ and $R_2$ are both methyl, $R_3$ is hydrogen, and $R_4$ is 2-dimethylaminoethylamino; 1,4,5-tris[(2-dimethylaminoethyl)amino]-8-hydroxyanthraquinone.

4. The compound according to claim 1 wherein $R_1$ and $R_2$ are both hydrogen, $R_3$ is hydroxy, and $R_4$ is hydrogen; 1,4-bis[(2-aminoethyl)amino]-5,6-dihydroxyanthraquinone.

5. The compound according to claim 2 wherein $R_1$ and $R_2$ are both ethyl, $R_3$ is hydrogen, and $R_4$ is 2-diethylaminoethylamino; leuco-1,4,5-tris[(2-diethylaminoethyl)amino]-8-hydroxyanthraquinone.

6. The compound according to claim 2 wherein $R_1$ is hydrogen, $R_2$ is ethyl, $R_3$ is hydroxy, and $R_4$ is hydrogen; leuco-1,4-bis[(2-ethylaminoethyl)amino]-5,6-dihydroxyanthraquinone.

* * * * *